United States Patent
Laukkanen et al.

(10) Patent No.: US 9,833,540 B2
(45) Date of Patent: Dec. 5, 2017

(54) NANOFIBRILLAR POLYSACCHARIDE FOR USE IN THE CONTROL AND PREVENTION OF CONTRACTION AND SCARRING

(71) Applicant: UPM-KYMMENE CORPORATION, Helsinki (FI)

(72) Inventors: Antti Laukkanen, Helsinki (FI); Esko Kankuri, Helsinki (FI); Kristo Nuutila, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 14/767,857

(22) PCT Filed: Feb. 21, 2014

(86) PCT No.: PCT/FI2014/050131
§ 371 (c)(1),
(2) Date: Aug. 13, 2015

(87) PCT Pub. No.: WO2014/128354
PCT Pub. Date: Aug. 28, 2014

(65) Prior Publication Data
US 2015/0367024 A1    Dec. 24, 2015

(30) Foreign Application Priority Data
Feb. 22, 2013  (FI) ..................... 20135172

(51) Int. Cl.
*A61L 15/28*    (2006.01)
*A61L 15/60*    (2006.01)
*A61L 26/00*    (2006.01)

(52) U.S. Cl.
CPC ........... *A61L 26/0023* (2013.01); *A61L 15/28* (2013.01); *A61L 15/60* (2013.01); *A61L 26/008* (2013.01); *A61L 26/009* (2013.01); *A61L 26/0066* (2013.01); *A61L 2300/00* (2013.01); *A61L 2300/23* (2013.01); *A61L 2400/12* (2013.01); *A61L 2430/10* (2013.01); *A61L 2430/34* (2013.01)

(58) Field of Classification Search
CPC ..... C08L 1/16; C08L 5/08; C08L 1/02; A61K 2300/00; A61K 38/1841; A61K 35/28; A61K 47/38; A61K 9/0024; A61K 9/06; A61L 27/26; A61L 2430/06; A61L 27/3834; A61L 27/52; C12N 2533/72; C12N 2533/78
See application file for complete search history.

(56) References Cited

U.S. PATENT DOCUMENTS

2011/0274742 A1* 11/2011 Arinzeh .................. A61L 27/26
424/443

FOREIGN PATENT DOCUMENTS

| WO | WO2008/010199 A2 * | 1/2008 | ............... D01D 5/00 |
| WO | 2011/134957 A1 | 11/2011 | |
| WO | 2012/056109 A2 | 5/2012 | |
| WO | 2012/106707 A2 | 8/2012 | |
| WO | WO2012/106707 A2 * | 8/2012 | ............. A61L 33/00 |

OTHER PUBLICATIONS

Muzzarelli et al. ("Chitin nanofibrils/chitosan glycolate composites as wound medicaments", Carbohydrate polymers, 70, 274-284, 2007.*
Ferereira ("Proliferation of fibroblasts cultured on a hemi-cellulose dressing", Journal of Plastic, Reconstructive, and Aesthetic Surgery, 63, 865-869, 2010).*
Muzzarelli et al., "Chitin nanofribrlslchitosan glycolate composites as wound medicaments", Carbohydrate Polymers 70:274-284 (2007).

* cited by examiner

*Primary Examiner* — Audrea Buckley
(74) *Attorney, Agent, or Firm* — Nixon Peabody LLP

(57) ABSTRACT

The present invention relates to nanofibrillar polysaccharide hydrogels for use in the prevention and control of scarring and contraction in connection with wound healing or tissue repair.

19 Claims, 8 Drawing Sheets

NANOFIBRILLAR POLYSACCHARIDE FOR USE IN THE CONTROL AND PREVENTION OF CONTRACTION AND SCARRING

CROSS-REFERENCE TO RELATED APPLICATIONS

This application is a National Phase Entry Application under 35 U.S.C. §371 of International Application No. PCT/FI2014/050131 filed Feb. 21, 2014, and claims priority under 35 U.S.C. §119 of Finnish Application No. 20135172 filed Feb. 22, 2013, the contents of which are incorporated herein by reference in their entireties.

FIELD OF THE INVENTION

The present invention relates generally to wound treatment, wound healing and tissue repair, and to methods useful in wound treatment, wound healing and tissue repair. More particularly, the invention relates to agents and compositions comprising nanofibrillar polysaccharide, useful in the control and prevention of scarring and contraction typically associated with wound healing and tissue repair. The present invention further relates to nanofibrillar polysaccharide incorporated in a hydrogel, for use in the control and prevention of scarring and contraction associated with wound healing and tissue repair.

BACKGROUND OF THE INVENTION

Treatment of wounds, particularly of more severe wounds is often very challenging. Contraction is generally regarded as a natural and essential component for wound healing. However, in many cases excessive and uncontrolled wound contraction can be observed as well as contraction induced fibrosis, which can lead to disfigurement and loss of function. Fibrosis or fibrous tissue contraction can also occur during tendon repair. This leads to shortening of tendons and/or reduction in tensile strength.

The reconstitution of tissue structural integrity in higher vertebrate animals following, for example, surgical or accidental trauma, involves a broadly understood pattern of repair or wound closure. Examples of cutaneous wounds include burn wounds, neuropathic ulcers, pressure sores, venous stasis ulcers, and diabetic ulcers. Open cutaneous wounds heal routinely by a repair process that includes six major components: (1) inflammation; (2) fibroblast proliferation; (3) blood vessel proliferation; (4) connective tissue synthesis; (5) epithelialization; and (6) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age.

The reparative process begins with the recruitment of a variety of specialized cells to the effected tissue and involves extracellular matrix and basement membrane deposition, angiogenesis, selective protease activity and re-epithelialization. An important component of the healing process in adult mammals is the stimulation of fibroblasts to generate the extracellular matrix. This extracellular matrix constitutes a major component of the connective tissue which develops to repair a wound area. The repair process, however, is not perfect and the connective tissue is often fibrous in nature and commonly forms into a connective tissue scar (a process known as fibrosis). Scars are composed of a connective tissue which is predominately a matrix of collagen types 1 and 3 and fibronectin. The scar may consist of collagen fibers in an abnormal organization (as seen in scars of the skin) or it may be an abnormal accumulation of connective tissue (as seen in scars of the central nervous system). Most scars consist of abnormally organized collagen and also excess collagen.

A cutaneous or dermal scar may be defined as the macroscopic disturbance of normal skin structure and function arising as a consequence of wound repair.

In man, in the skin, scars may be depressed below the surface or elevated above the surface of the skin. Hypertrophic scars are a more severe form of normal scarring and are elevated above the normal surface of the skin and contain excessive collagen arranged in an abnormal pattern. A keloid is another form of pathological scarring which is not only elevated above the surface of the skin but also extends beyond the boundaries of the original injury. In a keloid there is excessive connective tissue which is organized in an abnormal fashion predominately in whirls of collagenous tissue. Examples of such situations are scars of the skin where excessive scarring may be detrimental to tissue function and particularly when scar contracture occurs (for instance skin burns and wounds which impair flexibility of a joint). In the skin, hypertrophic or keloid scars can cause functional and cosmetic impairment and there is a need to prevent their occurrence. Scarring resulting from the use of skin grafts, in both donor and recipient sites, and from the application of artificial skin, can also be problematic and needs to be minimized or prevented.

Various agents, wound dressings, lyophilized pig skin, composites and methods have been proposed in the art for applications in the field of wound treatment. Wound dressings and ointment gauzes are generally used as therapy for a skin defect reaching to an upper layer of dermis, such as a superficial dermal burn. When a skin defect reaches to a lower layer of dermis, such as a deep dermal burn, a dermal burn or a decubitus in at least the second grade, self-reconstruction in a cutaneous tissue by proliferation of epidermal cells is usually problematic. These defects are typically treated by debriding a slough or an abnormal granulation tissue, reconstructing a normal granulation tissue by covering the defect with an allogeneic skin, xenogeneic skin, artificial silicon skin, skin replacement products, wound dressings or the like, and reconstructing a skin by performing skin graft. Skin grafts have been used in general to resurface superficial defects of many kinds.

A split-thickness graft (STSG) contains epidermis and a variable amount of dermis. A full-thickness graft (FTSG) includes all of the dermis and the epidermis. The graft may be an autograph taken from another part of the same individual, an isograph taken from a genetically identical donor, an allograph taken from another individual of the same species or a xenograph taken from an individual of different species. In the treatment of deep burn wounds that require excision, autologous split-thickness skin grafting (STSG) is the standard treatment today. The amount of dermis included with the graft determines both the likelihood of survival and the level of contracture.

Treatment with skin grafts, such as STSGs is, however, not without problems. In ideal conditions, having a healthy wound bed and in the absence of infections, a STSG will adhere or "take" well, however, in many cases the conditions may be far from ideal. For example the wound bed may bleed, be infected, it may contain wound excretion, epithelisation may be weakened, due to shear force, or the thickness of the STSG is not suitable, which all may significantly impair the "take" and healing process.

A skin graft begins to shrink immediately after harvest. As a result of primary contraction the skin graft may lose from about 40% to about 10% of its original area. After transfer to a recipient site, the skin graft will shrink as it heals; this is understood as secondary contraction. FTSGs tend to remain the same size after significant primary contraction, but STSGs contract whenever the circumstances allow. STSGs have greater likelihood of secondary contracture, and particularly thinner STSGs tend to shrink considerably and pigment abnormally. Dermis has contraction-inhibiting effect and the greater the proportion of dermis in the graft, the greater the inhibition and the less the graft will contract. Thus high contraction rates are typically associated particularly with thin STSGs.

With the STSGs dermal appendages, such as hair follicles largely remain intact at the donor site permitting stem cell activation and epidermis resurfacing from these niches. The graft donor sites thus typically heal within about three weeks to permit re-harvesting of the same site that is essential in the treatment of large burns. For covering large wound areas STSGs can be meshed to enable graft expansion, usually in a 1:1.5 to 1:6 ratio. The interstices of the meshed graft heal by epithelial migration from the graft's edges.

Graft and wound contraction always occurs primarily at the outset and the process can continue for many months after the wound has healed. Ensuing fibrotic scar contracture can lead to restriction of the patient's movements as well as a poor cosmetic result. All healed burns as well as skin grafted burns therefore require intensive scar therapy after the acute phase in an attempt to prevent scar formation and contracture problems.

Contraction and fibrosis may also result from rejection occurring particularly in connection with the use of allogeneic skin or xenogeneic skin grafts.

In a similar manner contraction occurs also in connection with the treatment and healing of mucous membranes. Particularly problematic areas are mucous membranes, skin areas with very thin epithelium, such as eyelids, and large burn wounds.

There is still at present neither a truly effective treatment available, nor a plausible method for the control and/or prevention of contraction. Additionally, the extent of fibrosis and contraction is unpredictable and in the more difficult cases reoperation and/or surgical release or removal of fibrotic tissue, as well as a further STSG transplantation may be required.

Whilst the above considerations mainly apply to contraction and fibrosis development in man, it will be appreciated that contraction and fibrosis can also be problematic in other animals, particularly in the veterinary field in the treatment of animals like domestic animals (e.g. horses, cattle, dogs, cats). Abdominal wounds are an example of one major reason for having to put down race horses.

Some pharmacological agents, such as beta-aminopropionitrilefumarate (beta-APN or BAPN-F), are used for inhibiting collagen crosslinking in veterinary medicine. There are also a number of post-scarring agents that attempt to treat the scar once formed.

Microbially produced cellulose gel, modified by bonding chemically or physically an animal cell adhesive protein to the cellulose, useful particularly in sheet form as artificial skin or vulnerable cover, is suggested in U.S. Pat. No. 5,558,861.

WO 2007/027849 describes the use of microbial nanocellulose as a substrate in wound healing systems, suitably in wound dressings. Said microbial nanocellulose is particularly multi-ribbon cellulose produced by specific *Glucono-acetobacter* strains. The dressing may additionally comprise one or more active substances, such as biologically active peptides, proteins, small molecules, lipids etc., and it may also be formed into a suture, sheet, compress, bandage, band, prosthesis, fiber, woven fiber, bead, strip or gauze.

US 2007/0231271 relates to a topical composition in gel form, comprising bacterial cellulose paste, gel-forming cellulose derivative and propylene glycol, for the treatment of epithelial lesions, such as burns, abrasions, cuts, post-surgical wounds and ulcers. After application and drying of the composition a mechanical barrier, such as a film or membrane is formed protecting the injured area.

WO 2012107648 relates to external use of microfibrillated cellulose, in the form of aqueous gel, ointment foam etc., for the treatment of skin inflammations, atopic dermatitis, psoriasis and skin burns in general.

Publication US 2012231038 describes a biocompatible cellulose hydrogel membrane for wound treatment, particularly for ocular wounds. Said cellulose hydrogel membrane comprises cellulose, microcrystalline cellulose or microbial cellulose, obtained by activating cellulose, dissolving the activated cellulose and allowing the obtained solution to gel. Said hydrogel membrane has sufficient tensile strength and tear strength for wound treatment applications.

Despite the ongoing research and development, there is still a need to provide improved agents, compositions and methods for the prevention of contraction in connection with wound treatment, wound healing and tissue repair. Further, there is a need for methods, agents and compositions for the prevention the development of fibrosis.

SUMMARY OF THE INVENTION

An object of the invention is to provide new agents and compositions for use in the control and prevention of scarring and contraction in connection with wound treatment, wound healing and tissue repair.

Another object of the invention is a method for the control and prevention of scarring and contraction in connection with wound treatment, wound healing and tissue repair.

The present invention relates to nanofibrillar polysaccharides for use in the control and prevention of scarring and contraction, which is associated with wound treatment, wound healing and tissue repair.

Particularly the present invention relates to nanofibrillar polysaccharide hydrogels, for use in the control and prevention of scarring and contraction which is associated with wound treatment, wound healing and tissue repair.

The present invention also relates to the use of nanofibrillar polysaccharides in the prevention and control of scarring and contraction in connection with wound healing or tissue repair, wherein said nanofibrillar polysaccharides are incorporated in a hydrogel.

The present invention also relates to an applicator device comprising the nanofibrillar polysaccharide hydrogel.

The present invention also relates to a method for the control and prevention of scarring and contraction in connection with wound healing or tissue repair, in a subject in need thereof, said method comprising contacting the wound or mucous membrane or tissue with an effective amount of a nanofibrillar polysaccharide hydrogel.

Nanofibrillar polysaccharide hydrogel will find particular use in the control and prevention of scarring and contraction in connection with wound treatment, wound healing and tissue repair. Said wounds may be caused by laser surgery, burns, cancer treatments, radiation, biopsy excision sites, scars from pathogens, traumatic wounds, entry wounds, cosmetic surgery, reconstructive surgery and the like, as well as chronic wounds and ulcers etc.

Characteristic features of the invention are provided in the appended claims.

Definitions

For the purposes of promoting an understanding of the principles of the invention, reference will now be made to certain embodiments and specific language will be used for describing the same. It will nevertheless be understood that no limitation of the scope of the invention is thereby intended, and alterations and modifications in the illustrated methods and agents, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

The term "contraction" is used herein to refer broadly to the phase of wound healing when the cells in the edges of a wound or in the granulation tissue migrate or contract to close the site of trauma, including scar contracture occurring as the scar matures.

As used herein, the term "wound" is used to refer broadly to injuries to the skin, mucous membrane, and subcutaneous tissue including tendons, initiated in different ways and with varying characteristics.

Wounds are generally classified into one of four grades depending on the depth of the wound:
Grade I: wounds limited to the epithelium;
Grade II: wounds extending into the dermis;
Grade III: wounds extending into the subcutaneous tissue; and
Grade IV or full-thickness wounds: wounds in which bones are exposed e.g., a bony pressure point such as the greater trochanter or the sacrum.

As used herein, the term "chronic wound" refers to a wound that has not healed within 30 days. Examples of chronic wounds are neuropathic ulcers, pressure sores, venous stasis ulcers, and ulcers caused by diabetes and its' complications.

As used herein the term "wound healing" or "cicatrisation" refers to an intricate process in which the skin or mucous membrane or another organ-tissue repairs itself after injury.

The classic model of wound healing is divided into three or four sequential, yet overlapping, phases: (1) hemostasis, (2) inflammatory, (3) proliferative and (4) remodeling phase. Within minutes post-injury, platelets (thrombocytes) aggregate at the injury site to form a fibrin clot, acting to control active bleeding (hemostasis). In the inflammatory phase, bacteria and debris are phagocytosed and removed, and factors are released that cause the migration and division of cells involved in the proliferative phase. In the proliferative phase angiogenesis, collagen deposition, granulation tissue formation, epithelialization, and wound contraction take place. In angiogenesis, new blood vessels are formed by vascular endothelial cells. In fibroplasia and granulation tissue formation, fibroblasts grow and form extracellular matrix by excreting collagen and fibronectin. Concurrently, re-epithelialization of the epidermis occurs, whereby epithelial cells proliferate and 'crawl' atop the wound bed, providing cover for the new tissue.

As used herein, the term "polysaccharide" is understood to encompass long linear or branched carbohydrate molecules of repeated monomer units joined together by glycosidic bonds, and complex carbohydrates composed of a chain of monosaccharides joined together by glycosidic bonds.

The term "nanofibrillar polysaccharide" refers to a collection of polysaccharide nanofibrils or nanofibril bundles. The term "nanofibrils" refers to existing substructures isolated from the polysaccharide raw material. As used herein, the term "nanofibrillar cellulose" or "NFC" is understood to encompass all microfibrillated celluloses (MFC) and nanocelluloses. Further, there are several other widely used synonyms for NFC, for example fibril cellulose, cellulose nanofiber, nanofibrillated cellulose (CNF), nano-scale fibrillated cellulose, microfibrillar cellulose, or cellulose microfibrils.

In addition, NFC produced by certain microbes has also various synonymes, for example, bacterial cellulose (BC), microbial cellulose (MC), biocellulose, nata de coco (NDC), or coco de nata (CDN).

DETAILED DESCRIPTION OF THE INVENTION

Figure 1:
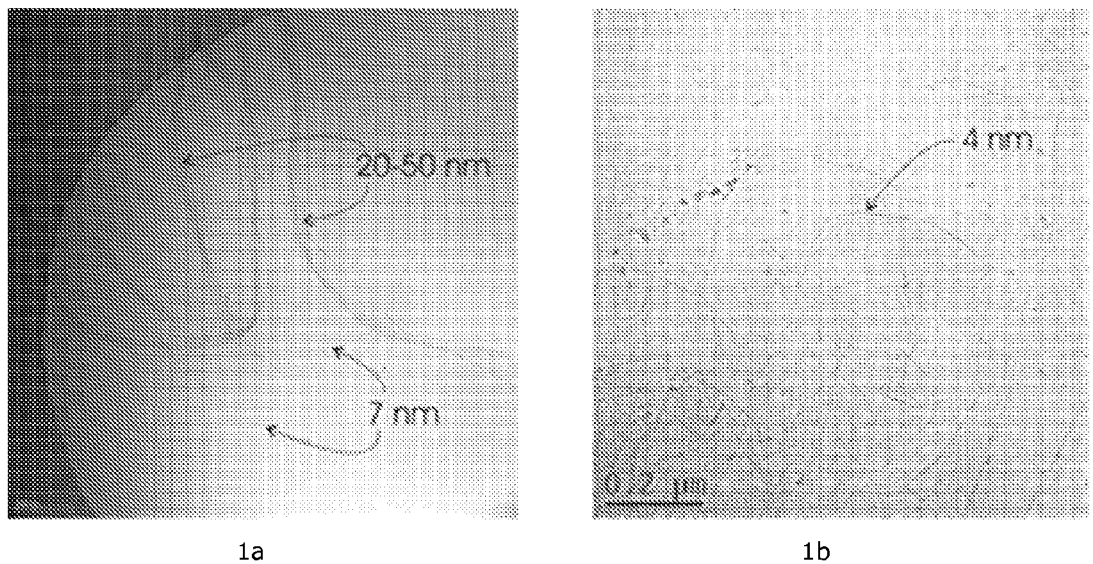
FIGS. 1 (1a and 1b) presents Cryo-TEM images of nanofibrillar cellulose hydrogels.

It was surprisingly found out that nanofibrillar polysaccharide, particularly nanofibrillar polysaccharide hydrogels have properties that are highly beneficial in the control and prevention of scarring and contraction typically occurring in connection with wound treatment, wound healing and tissue repair.

Often uncontrolled and/or too strong contraction, typically associated with processes occurring in connection with wound treatment, wound healing and tissue repair, is unfavourable and undesired. For example, in conjunction with large wounds and especially in association with treatment using skin grafts, contraction can lead to over-granulation, formation of fibrous tissue or scar that can be brittle, fragile, or limit movement, whereby reoperation and/or surgical release or removal of fibrotic tissue may be required. The nanofibrillar polysaccharide hydrogel effectively prevents and controls scarring as well as wound contraction and contraction of the skin grafts, such as split thickness skin graft (STSG), and it has no adverse effect on epithelialization. According to a preferable embodiment the nanofibrillar polysaccharide hydrogel particularly effectively prevents and controls contraction occurring in connection with wound treatment, wound healing and tissue repair.

Nanofibrillar polysaccharide provides the hydrogel a unique structure resembling closely the extracellular matrix.

Polysaccharides suitable for use in the present invention include celluloses, hemicelluloses, chitins, chitosans, alginates, pectins, arabinoxylans, and any derivatives thereof and any combinations thereof. Preferred polysaccharides are celluloses, chitins, chitosans, and any derivatives and combinations thereof.

The celluloses may be obtained from any cellulose raw material based on any plant material that contains cellulose, any microbial cellulose, or any cellulose raw material source that can be used in production of cellulose pulp, refined pulp, and NFC.

Plant material may be any wood derived or non-wood derived plant material. Said wood may be selected from softwood (SW) trees, such as spruce, pine, fir, larch, douglas-fir and hemlock, from hardwood (HW) trees, such as birch, aspen, poplar, alder, *eucalyptus* and *acacia*, and from mixtures of softwoods and hardwoods.

Said non-wood plant material may be selected from agricultural residues, grasses and other plant materials, such as straw, leaves, bark, seeds, hulls, flowers, vegetables and fruits, from cotton, corn, wheat, oat, rye, barley, rice, flax, hemp, manilla hemp, sisal hemp, jute, ramie, kenaf, bagasse, bamboo and reed.

The cellulose raw material may be also derived from cellulose-producing micro-organisms, such as materials obtained from bacterial fermentation processes. The micro-organisms may be selected from the genus *Acetobacter, Agrobacterium, Rhizobium, Pseudomonas* and *Alcaligenes*, suitably the genus *Acetobacter* and particularly suitably the species *Acetobacter xylinum* or *Acetobacter pasteurianus*. Cellulose may also be obtained from algae, for example cellulose can be found in structural walls of green algae, brown algae, most of the red algae and most of the golden algae.

The term "cellulose pulp" refers to cellulose fibers, which are isolated from any cellulose raw material, using chemical, mechanical, thermo-mechanical, or chemi-thermo-mechanical pulping processes. Particularly cellulose pulp, which can be pulp of plant origin, especially wood (SW or HW pulp, for example bleached birch pulp) and where the cellulose molecules are oxidized, is easy to disintegrate to NFC.

Chitin and chitosan having a (1,4)-β-N-acetyl glycosaminoglycan repeating structure and deacetylated derivatives thereof, respectively, may also be used. Chitin may be obtained from the exoskeletons of shellfish (crustaceans) and insects and cell walls of mushrooms. Purified chitin may conveniently be obtained from for example crabs and prawns using methods known in the art, where associated components such as matrix components, proteins, pigments, glucans and minerals may be removed. It may then be subjected to mechanical disintegration, utilizing for example equipment and methods described in connection with NFC below, in an aqueous medium to obtain slurry comprising chitin nanofibers having high aspect ratio and diameter typically of 10-40 nm.

Chitosan may be obtained from chitin using chemical modification methods known as such.

To obtain NFC with the desired properties and dimensions, mechanical disintegration of cellulose pulp, oxidized cellulose raw material, microbial cellulose etc is carried out with suitable equipment, such as a refiner, grinder, homogenizer, colloider, friction grinder, ultrasound-sonicator, fluidizer such as microfluidizer, macrofluidizer or fluidizer-type homogenizer. Thus NFC refers to mechanically disintegrated products. In a similar manner, using mechanical disintegration, also other nanofibrillar polysaccharides are obtained.

Several different grades (types) of NFCs have been developed using various production techniques. The grades have different properties depending on the manufacturing method, degree of fibrillation and chemical composition. The chemical compositions of the grades also vary. Depending on the raw material source, e.g. HW vs. SW pulp, different polysaccharide composition exists in the final NFC product. Typically, native or non-derivatized grades have larger diameters and wider fibril size distribution while the derivatized grades have smaller diameters and narrower size distributions.

Derivatized grades of NFC may be blended with native grade for enhancing binding of certain compounds to the gel or varying other properties etc.

NFC is understood to encompass here also any chemically or physically derivatized celluloses, cellulose nanofibers or nanofiber bundles. The chemical derivatization may be based for example on carboxymethylation, oxidation, (TEMPO-mediated oxidation), esterification, or etherification reaction of cellulose molecules. Anionic (including oxidized) and cationic grades are examples of chemically derivatized grades. Derivatization may also be realized by physical adsorption of anionic, cationic, or non-ionic substances or any combination of these on cellulose surface. The described derivatization can be carried out before, after, or during the production of NFC. Derivatized grades are typically prepared from bleached pulps. In the derivatized grades, any hemicelluloses present may also be derivatized together with the cellulose domain.

Suitably the cellulose raw material such as cellulose pulp is pretreated with acid and base prior to the mechanical disintegration. The pretreatment is effected by subjecting the cellulose pulp to acid treatment, preferably with hydrochloric acid for removing any positively charged ions having a charge more than +1, followed by treatment with an inorganic base containing positively charged ions having a charge+1, preferably NaOH, where Na⁺ ions replace the earlier ions. The absence of any positively charged ions having a charge more than +1 is particularly advantageous in life science applications where complex formation of DNA or proteins with ions having charges more than +1 can be avoided. The pretreatment provides the final product excellent gelling properties and improved transparency. The NFC obtained from pretreated cellulose raw material is referred to here as ion exchanged NFC and it contains sodium counter-ion. According to one embodiment of the invention ion exchanged native NFC is suitably used.

It is also important to minimize the microbial contamination of the product before and during the mechanical disintegration, such as fibrillation. For example, prior to fibrillation/mechanical disintegration, it is advantageous to aseptically collect the cellulose pulp from the pulp mill immediately after bleaching stage when the pulp is still sterile.

The nanofibrillar polysaccharides may comprise plant derived cellulose or microbial cellulose or cellulose analogues or any combination thereof. Particularly suitably said nanofibrillar polysaccharides are selected from plant derived native NFCs, anionic NFCs, native NFCs subjected to ion exchange treatment, chitin nanofibrils, chitosan nanofibrils and any combinations thereof.

Nanofibrillar polysaccharides have typically high aspect ratio. Nanofibrillar polysaccharide may comprise isolated nanofibrils and/or bundles formed of said nanofibrils. The smallest nanofibrils are similar to so called elementary fibrils, which are typically 2-12 nm in diameter. The dimensions of the nanofibrils or nanofibril bundles are dependent on raw material and disintegration method.

The nanofibrillar polysaccharides are characterized by very high water retention values, a high degree of chemical accessibility and the ability to form stable gels in water. The nanofibrillar polysaccharide is typically a dense network of highly fibrillated polysaccharides.

The number average diameter of nanofibrillar polysaccharide or nanofibrillar polysaccharide bundles may range between 1 and 500 nm, according to one suitable embodiment between 2 and 200 nm, according to another suitable embodiment between 2 and 100 nm, and according to a further suitable embodiment between 2 and 20 nm.

The number average diameter of native or non-derivatized nanofibrillar cellulose varies between 2-500 nm, preferably between 7 to 100 nm, and most preferably 7 to 50 nm. From Cryo-TEM images, also the bundled structure can be seen: the native grades are often mixtures of 7 nm elementary fibrils and 20-50 nm fibrillar bundles, as can be seen in FIG. 1 illustrating Cryo-TEM images of nanofibrillar cellulose hydrogels, opaque native (1a) and transparent anionic NFC (1b).

The derivatized NFCs are typically thinner, the number average diameter varying between 2 to 200 nm, preferably 2-20 nm, most preferably 2-6 nm.

The length of nanofibrillar cellulose is somewhat challenging to measure accurately, but rough estimates for length of native grade is between 1 to 100 micrometer, preferably 1-50, and most preferably 5-20 micrometers. The derivatized NFC are somewhat shorter; length varying between 0.3-50 micrometers, preferably 0.3-20 micrometers, and most preferably 0.5-10 micrometers. These values are estimated from CRYO-TEM, SEM or AFM images. The most accurate estimates are based on Cryo-TEM images.

Degree of fibrillation can be evaluated from fiber analysis where number of larger, only partially fibrillated, entities are evaluated. For example, in the case of derivatized nanofibrillar cellulose the number of those particles per mg of dry sample varies from 0 to 10000, preferably between 0 and 5000, most preferably between 0 and 1000. However, in non-derivatized NFC the number of non-fibrillated particles/mg is typically somewhat higher varying between 0 and 20000, preferably between 0 and 10000, and most preferably between 0 and 5000. The fiber analysis may suitably be carried out using FiberLab method as described below.

Fiber Analysis—FiberLab Method Description

Commercial fiber analyzers may be used, and suitable devices are for example fiber analyzers Kajaani FiberLab or FS-300. The sample preparation and measurement is carried out as instructed for typical fiber coarseness-measurement, with the following exceptions: Dry matter content (DMC) is determined by weighing a sample mass of minimum 8 g for dry matter content determination, heating until constant weight. Sample dilution is carried out as follows: Amount of sample to be diluted into 5 liter water vessel:
8 grams, if the DMC is around 2%.
16 grams, if the DMC is around 1%.
Pulp mixer is applied until all visible fibril bundles have disappeared.
Block removal—function is disabled.
A 50 ml sample is taken from the 5 liter vessel for the measurement. "Fibers per milligram" is calculated on the basis of the measurements:

$$FPM = ADF/(Mw*DMC/100*Vp/Vv), \text{where}$$

FPM=fiber per milligram [pcs/mg]
ADF=amount of fibers detected [pcs]
*This is the number of detected particles
Mw=amount of sample to be diluted into 5 liter water vessel [mg]
DMC=dry matter content of undiluted sample [%]
Vp=pipeted volume taken for the analyzer [ml]
Vv=volume of dilution vessel [ml].

Optical properties of different types of NFC hydrogels can be evaluated by turbidity measurements of dilute NFC hydrogels. Typically, hydrogels made from the derivatized NFC materials are more transparent when compared to non-derivatized grades due to smaller fibril diameters. For derivatized NFC, the turbidity varies between 3 and 150 NTU, preferably between 5 and 90 NTU, most preferably between 20 and 60 NTU. Turbidity of the non-derivatized NFC varies between 20 and 700 NTU, preferably between 40 and 500 NTU, most preferably between 90 and 200 NTU. The turbidity is measured suitably with a turbidometric method. Below a method based on nephelomethry is presented for measuring the turbidity of NFC samples, and results obtained with different grades of NFC.

Turbidity Measurement

Turbidometric methods based on nephelometry may suitably be used for turbidity measurements and an example of such method is presented as follows, for measuring the turbidity of NFC samples.

HACH P2100 Turbidometer, with a 50 ml measuring vessel, using 1 cm light path and 0.1% sample concentration, calculated on dry matter may be used for turbidity measurements. The calibration of the apparatus is checked and controlled with standard calibration bottles/samples.

The dry matter of the NFC sample is determined and 0.5 g of the sample (corresponds to 0.1%), calculated as dry matter, is loaded in the measuring vessel, which is filled with tap water to 500 g and vigorously mixed by shaking for about 30 s. Without delay the aqueous mixture is divided into 5 measuring vessels, which were inserted in the turbidometer. Three measurements on each vessel are suitably carried out. Mean value and standard deviation are calculated for each sample.

The degree of substitution in the chemical derivatization process can vary broadly. For example, TEMPO or N-oxyl mediated oxidation is typically conducted to charge values between 300 to 1500 micromol/g, preferably 600 to 1200 micromol/g, most preferably 700-1100 micromol/g. The oxidized NFC may contain also aldehyde functional groups, typically between 0 to 250 micromol/g. Derivatization via carboxymethylation is typically conducted for cellulose pulp to ds levels between 0.05 to 0.3, preferably between 0.08-0.25, most preferably 0.10-0.2 prior to fibrillation. If the derivatization is conducted by cationization, the ds levels are typically between 0.05 and 0.4, preferably 0.15-0.3.

The stiffness of the NFC hydrogels can be evaluated from viscoelastic measurements of the gels. Typically the storage modulus for 0.5% (by weight) nanofibrillar cellulose hydrogel in pure water at pH 7 at 25° C. is between 1 to 50 Pa, preferably 3 to 20 Pa. Often the derivatized NFC builds up stiffer hydrogels, but extensive fibrillation of these grades may lead also to lower storage modulus.

Rheological properties of nanofibrillar polysaccharide hydrogels can be also evaluated by monitoring viscosity as a function of shear stress or shear rate. The nanofibrillar polysaccharide hydrogels show plastic behaviour, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. Zero-shear viscosity values varies typically between 100 and 100 000 Pa s, preferably 5000 and 50 000 Pa s, in water at 0.5 wt % concentration. For non-derivatized NFC the preferable range is between 1000 and 10 000 Pa s. The yield stress varies typically between 0.1 and 50 Pa, preferably between 2 and 15 Pa, in water at 0.5 wt % concentration. Viscoelastic properties of nanofibrillar chitin and chitosan hydrogels resemble the situation with cellulose nanofiber hydrogels.

Rheological measurements of the NFC hydrogel are suitably carried out at room temperature at pH 7 with a stress controlled rotational rheometer (AR-G2, TA instruments, UK) equipped with four-bladed vane geometry. The diameters of the cylindrical sample cup and the vane are 30 mm and 28 mm, respectively. The length of the vane is 42 mm. The viscoelastic properties of the hydrogel are determined with a frequency sweep and a time sweep in dynamic oscillatory mode of the rheometer at a strain of 0.1 wt %. All samples are mixed, suitably with Waring blender prior to measurements (3 times 10 s).

Hydrogel Composition

The nanofibrillar polysaccharide hydrogel refers here to an aqueous dispersion comprising nanofibrillar polysaccharides. A gel is formed already at a low consistency in an aqueous medium. The gel is suitably transparent.

The nanofibrillar polysaccharide hydrogel with desired viscosity may be formed by blending the nanofibrillar polysaccharide in an aqueous medium, such as water. Any suitable mixing or blending apparatus may be used. However, the efficacy of the mixing may influence to fine structure of the gel, i.e. more homogeneous gels are obtained with more efficient mixing apparatus.

Microbial purity of the nanofibrillar polysaccharide hydrogel is essential. Therefore, the nanofibrillar polysaccharide hydrogel may be sterilized prior to use, suitably using any suitable sterilization method known in the art.

It is also advantageous that the product is pyrogen-free and contains no protein residues etc.

The composition may comprise from 0.01 to 30 wt %, suitably from 0.01 to 20 wt % of nanofibrillar polysaccharides or any combinations thereof. Suitably said composition comprises from 0.05 to 5 wt %, particularly suitably from 0.07 to 4 wt %, even more suitably 0.1 to 3 wt % of nanofibrillar polysaccharide or any combinations thereof.

For example NFC having number average diameter of 2-40 nm provides transparency to the hydrogel.

The water used in the hydrogel may suitably be purified water or sterilized water, preferably purified pyrogen-free water.

The stiffness of the NFC hydrogels reflects also ease of spreading of the hydrogels. Typically the storage modulus for 0.5% nanofibrillar cellulose hydrogel in pure water at pH 7 at 25° C. is between 1 to 50 Pa, preferably 1 to 20 Pa. Often the derivatized NFC builds up stiffer hydrogels, but extensive fibrillation of these grades may lead also to lower storage modulus.

The nanofibrillar polysaccharides may comprise plant derived NFC or microbial NFC or chitin nanofibril or chitosan nanofibrils or cellulose analogues or any combination thereof. Particularly suitably said nanofibrillar polysaccharides are selected from plant derived native NFCs, anionic NFCs, native NFCs subjected to ion exchange treatment, chitin nanofibrils and chitosan nanofibrils and any combinations thereof.

Optional Ingredients

The composition or agent may optionally comprise one or more bioactive agents. Said bioactive agent refers to a molecule or compound which exerts a physiological, therapeutic or diagnostic effect in vivo. Representative examples of bioactive agents include proteins, peptides, carbohydrates, lipids, nucleic acids and fragments thereof, anti-viral compounds, anti-inflammatory compounds, antibiotic compounds such as antifungal and antibacterial compounds, cell differentiating agents, analgesics, contrast agents for medical diagnostic imaging, enzymes, cytokines, anaesthetics, antihistamines, agents that act on the immune system i.e. immuno modulators, hemostatic agents, hormones, angiogenic or anti-angiogenic agents, neurotransmitters, therapeutic oligonucleotides, viral particles, vectors, growth factors, retinoids, cell adhesion factors, extracellular matrix glycoproteins, osteogenic factors, antibodies and antigens, steroids and painkillers. The bioactive agents can be in their free base or acid form, or in the form of salts, esters, or any other pharmacologically acceptable derivatives, enantiomerically pure forms, tautomers or as components of molecular complexes. The amount of bioactive agents in the composition can vary depending on the particular bioactive agent, the desired effect, and the time span for which the composition is to be administered.

Examples of classes of antibiotics that can be included in the composition include aminoglycosides (e.g., tobramycin, amikacin, gentamicin, kanamycin, netilmicin, tobramycin, streptomycin, azithromycin, clarithromycin, erythromycin, neomycin, erythromycin estolate/ethylsuccinate, gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), cephalosporins (e.g., cephalothin, cefazolin, cefaclor, cefamandole, cefoxitin, cefuroxime, cefonicid, cefinetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin), fluoroquinolones (e.g., ciprofloxacin), carbepenems (e.g., imipenem), tetracyclines (e.g., doxycycline, minocycline, tetracycline), macrolides (e.g., erythromycin and clarithromycin), monobactams (e.g., aztreonam), quinolones (e.g., fleroxacin, nalidixic acid, norfloxacin, ciprofloxacin, ofloxacin, enoxacin, lomefloxacin and cinoxacin), glycopeptides (e.g., vancomycin, teicoplanin), chloramphenicol, clindamycin, trimethoprim, sulfamethoxazole, nitrofurantoin, rifampin and mupirocin, and polymyxins, such as PMB, oxazolidinones, imidazoles (e.g., miconazole, ketoconazole, clotrimazole, econazole, omoconazole, bifonazole, butoconazole, fenticonazole, isoconazole, oxiconazole, sertaconazole, sulconazole and tioconazole), triazoles (e.g., fluconazole, itraconazole, isavuconazole, ravuconazole, posaconazole, voriconazole, terconazole and albaconazole), thiazoles (e.g., abafungin), and allylamines (e.g., terbinafine, naftifine and butenafine), echinocandins (e.g., anidulafungin, caspofungin and micafungin). Other antibiotics can include polygodial, benzoic acid, ciclopirox, tolnaftate, undecylenic acid, flucytosine or 5-fluorocytosine, griseofulvin, and haloprogin.

Examples of antimicrobial agents that can be included in the composition include silver particles, particularly silver nanoparticles, agents or compounds that release silver ions, chlorhexidine gluconate, and polyhexamethylene biguanide.

Examples of anesthetics that can be included in the composition include procaine, benzocaine, chloroprocaine, cocaine, cyclomethycaine, dimethocaine, piperocaine, propoxycaine, procaine, novocaine, proparacaine, tetracaine, lidocaine, articaine, bupivacaine, cinchocaine, etidocaine, levobupivacaine, mepivacaine, prilocaine, ropivacaine, and trimecaine. In some embodiments, the anesthetic is a combination of lidocaine and prilocaine.

Examples of analgesics that can be included in the composition include opiates and analogues thereof. Exemplary opiates include morphine, codeine, oxycodone, hydrocodone, dihydromorphine, pethidine, buprenorphine, tramadol, fentanyl and venlafaxine.

An example of hemostatic agents that can be included in the composition is thrombin. Examples of anti-inflammatory compounds that can be included in the composition include hydrocortisone, cortisone, dexamethasone, fluocinolone, triamcinolone, medrysone, prednisolone, flurandrenolide, prednisone, halcinonide, methylprednisolone, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, acetosalicylic acid, salicylic acid, diflunisal, methyl salicylate, phenylbutazone, sulindac, mefenamic acid, meclofenamate sodium and tolmetin.

Examples of antihistamines that can be included in the composition include diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine and chlorpheniramine.

Examples of growth factors that can be included in the composition, include vascular endothelial growth factor ("VEGF"), nerve growth factor, such as NGF-beta, platelet-derived growth factor (PDGF), fibroblast growth factors, including, for instance, aFGF and bFGF, epidermal growth factor (EGF), keratinocyte growth factor, tumor necrosis factor (TGF), transforming growth factors (TGF), including, among others, TGF-alpha and TGF-beta, including TGF-beta1, TGF-beta2, TGF-beta3, TGF-beta4, or TGF-beta5, insulin-like growth factors-I and -II (IGF-I and IGF-II), des(1-3)-IGF-I (brain IGF-I), neurotrophin-3 (NT-3) and brain-derived neurotrophic factor (BDNF).

Examples of immunomodulators that can be included in the composition include cyclosporin A, guanylhydrazone, azathioprine, methotrexate, cycphosphamide and tacrolimus.

The composition or agent may optionally comprise cells. The cells can be of any cell type, and they can include stem cells, undifferentiated cells, precursor cells, as well as fully differentiated cells and combinations thereof. In some embodiments, the cells comprise cell types selected from the group consisting of keratocytes, keratinocytes, fibroblast cells, epithelial cells and combinations thereof. In some embodiments, the cells are selected from the group consisting of stem cells, progenitor cells, precursor cells, connective tissue cells, epithelial cells, muscle cells, neuronal cells, endothelial cells, fibroblasts, keratinocytes, smooth muscle cells, stromal cells, mesenchymal cells, immune system cells, hematopoietic cells, dendritic cells, hair follicle cells and combinations thereof. In some embodiments, the cells from the wound site use the composition, particularly the hydrogel as a scaffold to grow and migrate in the wound bed. Bioactive agents can be added to the composition to affect various activities or properties of the cells, such as cell growth and proliferation, cell adhesion, differentiation, migration, maintenance of undifferentiated states, secretion of extracellular matrix, and secretion of molecules, including growth factors, prostaglandins, cytokines and the like.

In some embodiments, the composition may optionally include nutritional agents, such as vitamins, essential and non-essential amino acids, essential and non-essential fats and combinations thereof, hyaluronic acid, derivatives of hyaluronic acid, Aloe vera gel, propylene glycol, [beta]-1, 3-glucan, and buffer substances for maintaining the pH of the composition in the range from 4 to 9.

The nanofibrillar polysaccharide hydrogel may optionally have a backing material attached thereto. In some embodiments, the backing material provides additional protection and/or support. In some embodiments, the backing can serve to prevent visual observation of the wound through the transparent cellulose hydrogel, especially in situations where it is not desirable for the wound to be visible (or for the eye to be exposed to light). In some embodiments, the backing is not permanent, and can be freely removable and can be reattached, if needed. For example, in some embodiments, the backing can be removed by a health care provider to assess the progress of wound healing by inspecting the wound through the cellulose hydrogel membrane. In some embodiments, the backing may be in the form of a layer or more of cellulose (e.g., microbial or plant-based), a polyester, a polyurethane, a polyethylene glycol or derivative thereof, a vinyl pyrrolidone acrylic, a methacrylic acid, a silicone isobutylene, a isoprene or a styrene or combinations thereof.

The nanofibrillar polysaccharide hydrogel may optionally be incorporated in a support, such as gauze or non-woven material.

The nanofibrillar polysaccharide hydrogel may be incorporated or packed in application device, such as syringe, applicator, pump or tube containing the desired amount of the hydrogel, such as syringes of the size from 0.5 ml to 200 ml or even more. Said device may comprise a mouthpiece or nozzle providing constant flow of the hydrogel in desired thickness and breadth and geometrics. These "ready for use"

devices can be packed, sterilized and stored, and used when desired. These application devices may be incorporated in ready-to use kits.

The invention further provides methods of controlling and preventing contraction in connection with wound treatment, wound healing and tissue repair, in a subject in need thereof, comprising contacting the wound or mucous membrane or tissue with an effective amount of a nanofibrillar polysaccharide hydrogel of the invention.

The invention further provides methods for the control and prevention of the development of fibrosis in connection with wound treatment, wound healing and tissue repair, in a subject in need thereof, comprising contacting the wound or mucous membrane or tissue with an effective amount of a nanofibrillar polysaccharide hydrogel of the invention.

Examples of wound and tissue types for which the composition of the invention may be used include, but are not limited to, skin wounds, burn wounds, chronic wounds, wounds in mucous membranes and ulcers as well as tendon wounds. Additional examples of wounds include wounds caused by laser surgery, radiation, chemical burns, cancer treatments, biopsy excision sites, pathogens, gunshot or knife stabbings, cosmetic surgery and reconstructive surgery and the like. Ulcers include neuropathic ulcers, pressure sores, venous stasis ulcers, and diabetic ulcers and the like.

Suitably the nanofibrillar polysaccharide hydrogel may be used for the treatment of donor (sites that the physician uses for harvesting skin for grafting) and recipient sites in connection with therapy involving skin grafts, such as STSG and FTSG therapy.

Said nanofibrillar polysaccharide hydrogel may particularly suitably be used in grade II and grade III wounds, in partial thickness wounds (e.g., second degree burns, surgical wounds or wounds which still have the most of the dermis intact which can regenerate from the wound site) as well as in more severe wounds of grade IV. The grafts may be meshed or recruited minced skin grafting or epidermal sheet grafting may be used. The nanofibrillar polysaccharide hydrogel may also find use in connection with flap technique.

In skin grafts any known fixation techniques and agents may be used for fixing the graft and the polysaccharide hydrogel may be applied directly to the graft without the need to use of dressings. However, if desired protective dressings may be used.

In diabetic patients there are systemic challenges, such as the presence of neuropathy, endothelial dysfunction and increased susceptibility to infection, neuropathy because the patient is not in pain and often unaware of the severity of the wound until the infection spreads more proximally, often coupled with patient-specific obstacles, which make the care of chronic ulcerations in diabetic patients challenging. The nanofibrillar polysaccharide hydrogel may be used for improving the treatment of diabetic ulcers, particularly in connection with STSG therapy of chronic ulcers where sufficient hydration can be maintained, epithelialization is promoted, contraction is controlled and translocation of bacteria through it prevented.

Other suitable applications of the nanofibrillar polysaccharide hydrogel are in dermal over grafting, where a STSG is applied to a recipient bed or dermis or denuded scar tissue; in expanded grafts; in the treatment of unstable, depressed, corrugated or hypertrophic scars; in the treatment of unstable or hyperpigmented skin grafts, large pigmented nevi, radiation damage, vitiligo and removal of tattoos.

Particularly complex skin injuries are caused by burns, which result in an extensive damage to the various skin layers. Burns are generally defined according to depth and range from 1st degree (superficial) to $3^{rd}$ degree (entire destruction of epidermis and dermis). The standard protocol of burn management highlights several factors which accelerate the process of optimal healing: (a) control of fluid loss; (b) barrier to wound infection; (c) fast and effective wound closure, optimally with skin grafts or skin substitutes; and, (d) significant pain relief. The nanofibrillar polysaccharide hydrogel of the invention provides means for enhancing one or more of these factors.

The nanofibrillar polysaccharide hydrogels, suitably the ones comprising plant derived NFCs typically have remarkable high yield stress and high zero-shear viscosity at low concentrations. The hydrogels show shear-thinning behavior at higher shear rates, thus enabling easy dispensing of viscous hydrogels. When the hydrogels are sheared (e.g. in a rheometer or in a tube), the dispersed phase tends to move away from the solid boundaries, which leads to the creation of a lower-viscosity layer of liquid at the walls of the container. This phenomenon means that the resistance to flow, i.e. the viscosity is lower at the boundaries than in the bulk of the dispersion. Respectively, dispersing or injecting of the hydrogel to the wound with an applicator, such as syringe or pipette is easy even at higher concentrations (up to 4%), for providing an even and desired amount of the hydrogel to the wound, even of more complicated configuration or shape. Thus the hydrogel can be applied even to irregular, small and otherwise complicated wounds and wound beds evenly. The phenomenon enables also easy dispensing of the hydrogel with minimum disturbance of particles (bioactive components etc.) dispersed in said hydrogel.

The nanofibrillar polysaccharide hydrogel has excellent hydraulic permeability as well as diffusive permeability.

The nanofibrillar polysaccharide hydrogel provides close adhesion to the wound bed and good physical barrier to infection, thus preventing the entry of bacteria into the wound. Because the hydrogel is typically transparent, the wound can be inspected without the need to remove the hydrogel. Proteases are not able to degrade the hydrogel.

The nanofibrillar polysaccharide hydrogel may also easily be removed from the site of application (wound), for example with enzymes whereby enzymatic degradation of cellulose molecules is utilized. Proper enzymes are for example commercially available cellulases. Alternatively, the gel may also be diluted with an aqueous liquid (saline, purified water), followed by rinsing the hydrogel from the site (wound).

The nanofibrillar polysaccharide hydrogel may have the potential to stop the bleeding of wounds (hemostasis), and can include agents that promote clotting, such as thrombin.

If desired the nanofibrillar polysaccharide hydrogel, applied to the wound site, may be covered by a secondary dressing, film or membrane.

According to some embodiments, the nanofibrillar polysaccharide hydrogel enables growth of cells on or within the hydrogel to facilitate wound healing. The cells may be seeded into the hydrogel before or during the application of the hydrogel to the wound.

Also, said nanofibrillar polysaccharide hydrogels can be used as for closing the wound temporary in order to prevent wound contraction, bacterial contamination, and fluid loss. This provides an alternative for the temporary usage of allogeneic or xenogeneic skin grafts.

The nanofibrillar polysaccharide hydrogel can also be used in the intervention at the earliest possible time after the actual injury. It may be provided in sterile form as an immediate temporary cover for all types of injuries, including burns, physical wounding such as gunshots, knife cuts, bruises, contusions, lacerations, etc.

The nanofibrillar polysaccharide hydrogel allows an excellent penetration and molding to all contours of the wound and tissue and provides a proper moist environment.

Another interesting advantage of the nanofibrillar polysaccharide hydrogel includes its transparency or translucency, which allows for continuous clinical observation of the healing progress. It also facilitates the process of necrotic debris removal (autolytic debridement), improves the development of granulation tissue, accelerates the entire process of re-epithelialization and angiogenesis, and helps in keeping the wound base clean. The nanofibrillar polysaccharide hydrogel may easily and gently be rinsed off with water from the injury or wound and replaced with a fresh nanofibrillar polysaccharide hydrogel if necessary.

It promotes the process of optimal healing, and provides control of fluid loss, as well as a barrier for wound infection and effective wound closure without undesired contraction. Since the nerve endings are isolated, the pain of the injury is reduced. It finds also use in the treatment of chronic wounds and ulcers.

The findings presented in the Examples 3 and 4 indicate that the nanofibrillar polysaccharide hydrogel controls and inhibits contraction to a surprising extent, as can be seen particularly with STSG application. Thus the use of said nanofibrillar polysaccharide hydrogel, particularly comprising plant derived native NFC, helps preventing contraction and formation of contraction-induced fibrosis and movement restrictions when applying STSG therapy in patients. It was also observed that nanofibrillar polysaccharide has no negative effect on the epithelisation. No bacterial growth was observed during 2 to 4 weeks treatment with the nanofibrillar polysaccharide hydrogel. The wound site after healing comprises less scarring and contractions.

It was surprising that contraction could be controlled and prevented very efficiently, and simultaneously the diffusion of epithelial cells was not prevented. The nanofibrillar polysaccharide hydrogel provides also an ideal environment for granulation and re-epithelialization, and prevents translocation of bacteria through it. Myofibroblasts are known to contribute to wound contraction and scarring. Thus prevention of wound contraction can be understood to form part of the process where the hydrogel material prevents the phenotype change of fibroblasts to collagen actively depositing and wound contracting myofibroblasts.

The unique structure of the hydrogel is provided by the nanofibrillar polysaccharide, whereby said hydrogel is due to the rheological properties at the same time an easily spreadable product which fills all pockets and cavities, and on the other hand provides nanofibrillar network for the wound healing process.

Further, the properties particularly of plant derived NFC, such as anti-inflammatory effects, pyrogen free, free of chemical residues (particularly native NFC) provide further benefits to the invention.

The nanofibrillar polysaccharide hydrogel is also particularly suitable for donor site treatment as it provides suitable maintenance of hydration at the site, and it prevents contraction and translocation of bacteria through it and helps to control pain, optionally in combination with an anesthetic.

The nanofibrillar polysaccharide hydrogel is simple to use and apply at the desired site, thus required operating room time can be decreased. So far there has been no ideal donor site dressing or treatment available, for alleviating the pain and distress and providing optimal healing.

Further, the nanofibrillar polysaccharide hydrogel may be used in the treatment of tendon injuries and particularly for the control and prevention of contraction during tissue repair.

The nanofibrillar polysaccharide hydrogel may be used in the treatment of wounds in mucous membranes as well.

The nanofibrillar polysaccharide hydrogel is inert, non-allergenic, anti-inflammatory, non-toxic, non-pyrogenic, easy and inexpensive to manufacture and promotes natural host cellular migration to a wound site.

The nanofibrillar polysaccharide hydrogel is highly stable and it may be stored at any desired temperature and it can be sterilized.

Any of the embodiments discussed in this specification can be implemented with respect to a method, kit, reagent or composition.

The following examples are illustrative of embodiments of the present invention, as described above, and they are not meant to limit the invention in any way. The invention is illustrated also with reference to the figures.

EXAMPLES

The following hydrogel materials were used in wound healing experiments:

Opaque, Native, Non-Derivatized NFC Hydrogel
  Concentration 1.5 weight % in water
  Sterile, autoclaved
  Translucent or opaque, turbidity 139 NTU
  Slightly anionic surface charge, −2 mV
  Sodium counter ion
  Number average fiber diameter 7 nm nanofibers+20-50 nm fibril bundles, length several micrometers
  Number of un-fibrillated particles: 100-200 particles/mg, FiberLab method
  Carbohydrate composition: 72.8% glucose, 25.6% xylose, 1.4% mannose
  Fibrillated with industrial fluidizer (Microfluidics ltd.)
    Zero shear viscosity of 0.5 wt % sample 8 000 Pa s and yield stress 5 Pa.
    Zero shear viscosity of 1.0 wt % sample 30 000 Pa s and yield stress 20 Pa.
    Storage modulus of 0.5 wt % sample G'=10 Pa Transparent, Derivatized NFC Hydrogel
  TEMPO mediated oxidation prior to fibrillation, carboxylic acid content 1000 micromol/g
  Concentration 0.8 weight % in water
  Transparent, turbidity 10 NTU
  Highly anionic surface charge, −39 mV
  Number average fiber diameter 2-6 nm, length 500 nm-2000 nm
  Number of un-fibrillated particles 100 particles/mg, FiberLab method
  Carbohydrate composition: Raw material similar to native grade, but after modification the product contains also carbohydrate structures with carboxylic acid groups in C6 position.
  Fibrillated with industrial fluidizer (Microfluidics ltd.)
    Zero shear viscosity of 0.5 wt % sample 4 000 Pa s and yield stress 3 Pa.
    Zero shear viscosity of 0.8 wt % sample 35 000 Pa s and yield stress 22 Pa.
    Storage modulus of 0.5 wt % sample G'=5 Pa Cryo-TEM images of nanofibrillar cellulose hydrogels are presented in FIG. 1, opaque native (1a) and transparent anionic NFC (1b).

Purilon Hydrogel, Coloplast, Denmark (Comparative)
- Coloplast Purilon gel is a commonly used supplement in the treatment of various types of wounds to retain a moist wound environment.
- 10 wt % hydrogel
- Highly viscous mixture of water, sodium carboxymethylcellulose and calcium alginate
- Sterile
- Transparent
- Zero shear viscosity of 10 wt % sample 70 000 Pa s and yield stress 150 Pa.

Example 1

Flow Properties of Nanofibrillar Polysaccharide Hydrogels

The rheological flow properties of nanofibrillar polysaccharide hydrogels result in several features that are beneficial in the control and prevention of contraction in connection with wound treatment, wound healing and tissue repair. The hydrogels have a high viscosity at low shear (or rest) for optimum suspending capacity and mechanical stability, but they also show shear-thinning behavior at higher shear rates which enables easy dispensing and injection. The ability of nanofibrillar polysaccharide to provide these rheological properties was demonstrated in a test series where the viscosity of nanofibrillar polysaccharide hydrogel dispersions (hydrogels) was measured over a broad shear stress (rate) range in a rotational rheometer (AR-G2, TA Instruments, UK).

Figure 2A:
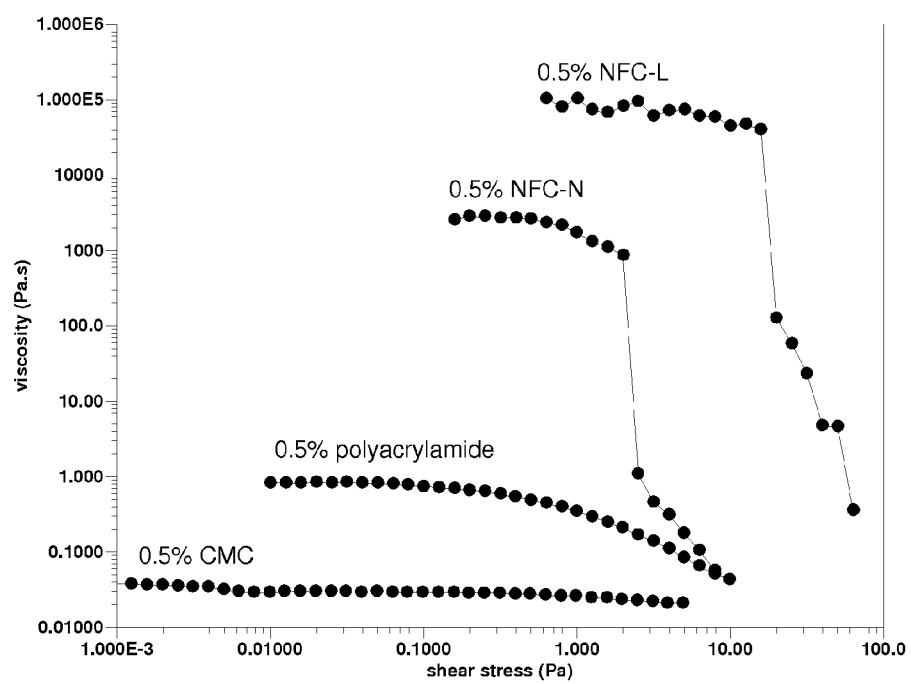
FIG. 2a shows the viscosity of 0.5% NFC dispersions as function of applied shear stress in comparison with 0.5% solution of water soluble polymers polyacrylamide (5 000 kDa) and CMC (250 kDa).

The nanofibrillar polysaccharide hydrogel dispersions show much higher zero-shear viscosities (the region of constant viscosity at small shear stresses) than other water soluble comparative polymers, as can be seen in FIG. 2a. In said figure the viscosity of 0.5% NFC dispersions as a function of applied shear stress in comparison with 0.5% solution of water soluble polymers polyacrylamide (5 000 kDa) and CMC (carboxymethylcellulose, 250 kDa) is presented. NFC-L stands for labilized NFC, here anionic NFC (nanofibrillated cellulose) oxidized by 2,2,6,6-tetramethylpiperidine-1-oxyl radical-mediated (TEMPO) oxidation, and NFC-N for native non-modified NFC subjected to ion exchange treatment, both being plant derived NFCs.

The zero-shear viscosity of NFC hydrogel is greatly increased by smaller nanofibril diameter induced by preceding labilization of the starting material, such as oxidation. The stress at which shear-thinning behavior starts ("yield stress") is also considerably high for the NFC hydrogels.

The suspending ability of a material is also the better, the higher the yield stress. In the case the hydrogel contains incorporated solid particles, such as silver particles, drug particles or transplanted cells, they are effectively stabilized against sedimentation by the combined effects of high zero-shear viscosity and high yield stress and high storage modulus. The gravitational force applied by the particles is much weaker than the yield stress. Thus, suspended cells are "frozen" inside the gel matrix when mixed with NFC hydrogel or "frozen" on the gel if deposited on the top of the gel.

Figure 2B:
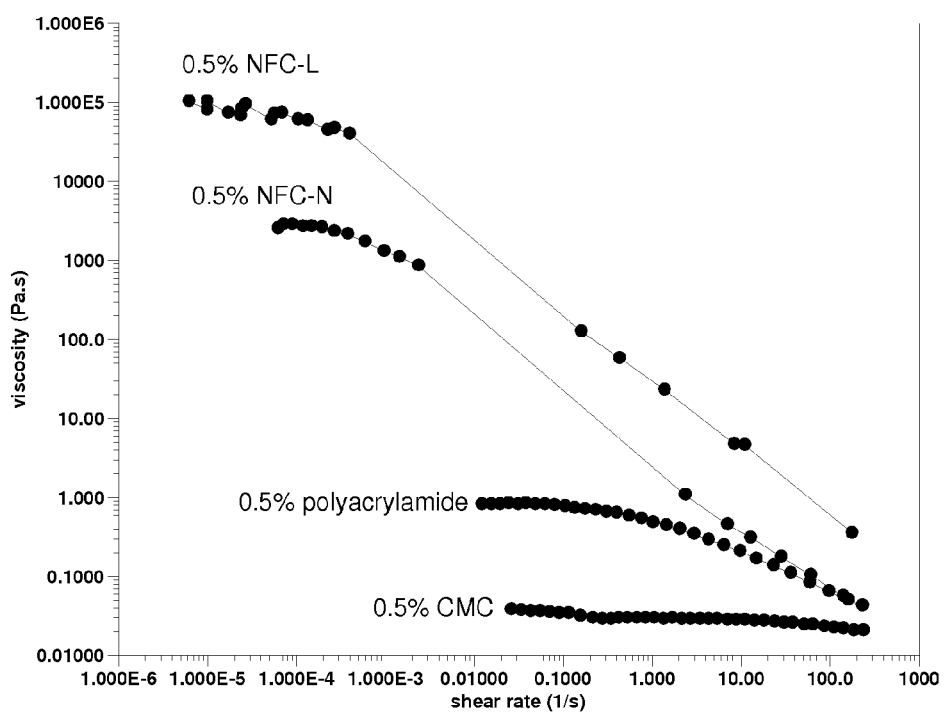
FIG. 2b presents the viscosity of 0.5% NFC dispersions as function of measured shear rate in comparison with 0.5% polyacrylamide and CMC.

In FIG. 2b the viscosity of the hydrogels is presented as a function of the measured shear rate. The viscosity of 0.5% NFC dispersions (plant derived NFC, same as in FIG. 2a) is presented as a function of measured shear rate in comparison with 0.5% polyacrylamide and CMC (carboxymethylcellulose). Typical shear rate region of different physical processes has been marked on the figure with arrows. From FIG. 2b it is obvious that the viscosity of the NFC dispersions drops at relatively small shear rates and reaches a similar level as that measured for the reference materials at shear rates of about 200 $s^{-1}$.

The network structure of NFC dispersion breaks down upon shearing. Upon the application of a certain stress, the viscosity of the system drops dramatically and a transition from solid-like to liquid-like behavior occurs. This kind of behavior is beneficial as it enables mixing of solid particles homogeneously into the NFC suspension by moderate mechanical shearing.

Figure 3:
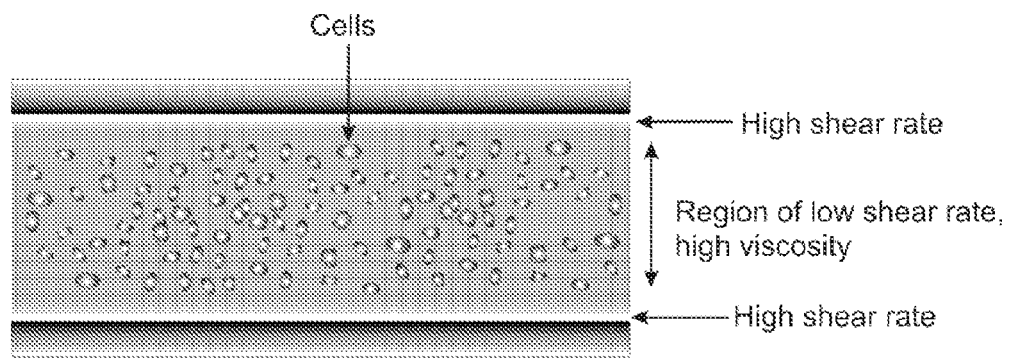
FIG. 3 shows a schematic presentation of a NFC dispersion containing cells dispersed therein, flowing in a needle.

When two-phase liquids, such as flocculated NFC dispersions, are sheared (e.g. in a rheometer or in a tube), the dispersed phase tends to move away from the solid boundaries, which leads to the creation of a lower-viscosity layer of liquid at the walls of the container (FIG. 3). This phenomenon means that the resistance to flow, i.e. the viscosity is lower at the boundaries than in the bulk of the dispersion.

Respectively, injection of the NFC hydrogel with a syringe and a needle or with pipette is easy even at high concentrations (1-4%). The phenomenon enables easy dispensing of the hydrogel, in this example cell suspensions with minimum disturbance of the cells, i.e. majority of the cells are located in the middle of the needle and are practically at rest. FIG. 3 provides a schematic presentation of a NFC dispersion (NFC-N used in FIG. 2a) containing cells dispersed therein, flowing in a needle.

Example 2

Diffusion in Nanofibrillar Polysaccharide Hydrogels

400 µl of 1% native or oxidized NFC hydrogel (anionic NFC oxidized by 2,2,6,6-tetramethylpiperidine-1-oxyl radical-mediated (TEMPO) oxidation, and native non-modified NFC subjected to ion exchange treatment, both being plant derived NFCs) was planted per filter on the apical compartment in Transwell™ filter well plates (filter pore size 0.4 µm). 1 ml of PBS was added into the basolateral side and 100 µl (25 µg) of fluorescent labeled dextrans were added on top of the hydrogels (MW of 20 k, 70 k and 250 k). Plate was fixed firmly and left undisturbed on a well plate rocker. 100 µl samples were taken from the basolateral side and equal amount was replaced with PBS. First samples were taken with 15 minute intervals, other samples were taken with different time points ranging from 30 minutes to 2 hours and final samples at 24 hours. Total of 168 samples were taken. Target plate (OptiPlate™-96 F) was measured at excitation and emission wavelengths 490 nm and 520 nm respectively.

Figure 4:
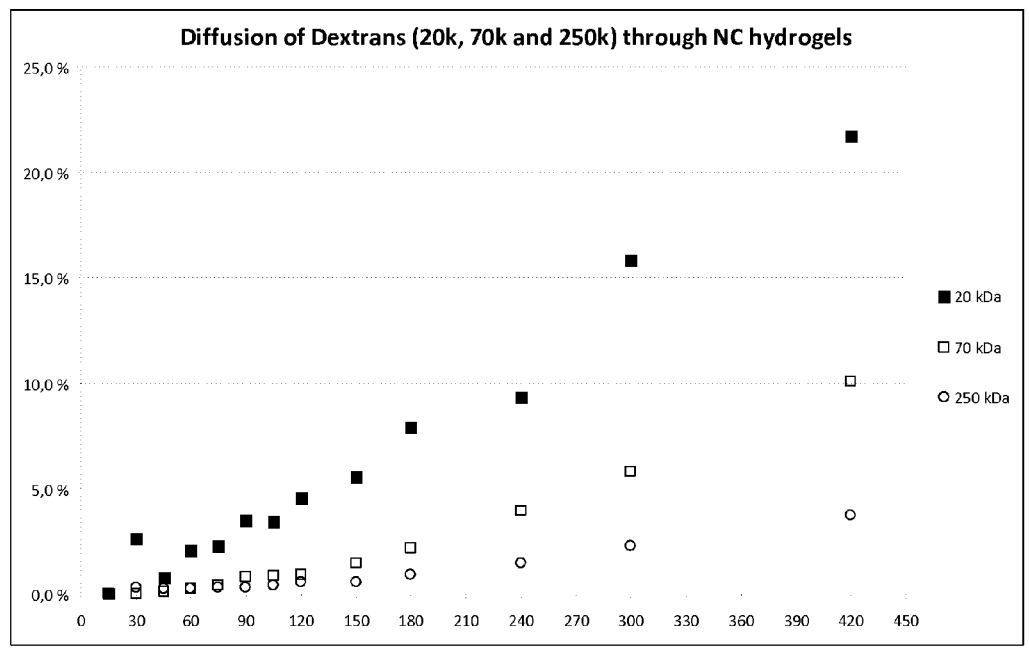
FIG. 4 shows diffusion of different molecular weight dextrans through 1% native NFC hydrogel.

FIG. 4 presents the diffusion of different molecular weight dextrans through 1% native NFC hydrogel. It is clear that different molecular weight model compounds are able to diffuse through the NFC hydrogel. The diffusion is dependent on molecular weight; smaller molecules diffuse faster than larger ones. Constant rate diffusion of molecules is beneficial feature for NFC hydrogels when used in wound healing treatments. Firstly, normal metabolites and nutrients diffuse freely in the boundary of the wound and the hydrogel. Secondly, drug molecules, silver ions, and secreted growth factors from transplanted cells are able to diffuse into the wound interface.

The free diffusion of molecules is especially beneficial in situations where the active compounds are slowly released from larger entities, which are stabilized into the gel due to high yield stress and zero-shear viscosity. Examples of this kind of situations are for example silver microparticles or nanoparticles which liberate silver ions into the hydrogel, or micronized weakly water-soluble drug particles, or cells producing beneficial compounds into the hydrogel.

Example 3

Effect of NFC Hydrogels in the Prevention of Contraction in Porcine Model

A porcine animal model was used to simulate third degree wounds.

Materials & Methods

Animals and Anesthesia

Pathogen-free 2-month-old domestic Landrace female pigs (18-26 kg) were used. The animals were anesthetized by intramuscular injection of ketamine (4-6 mg/kg s.c.) and medetomidine (0.5 mg/kg s.c.). Throughout the operation anesthesia was administered with intravenous infusion of propofol (4-10 mg $kg^{-1}$ $hr^{-1}$ i.v). The back of the pig was shaved, washed thoroughly and cleaned with chlorhexidine 0.5%.

Biopsy Wounds

Deep dermal wounds were made on the skin of the back with an 8-mm biopsy punch. NFC hydrogel (plant derived native non-modified NFC subjected to ion exchange treatment) was administered from a syringe to fill the wound cavity entirely. Untreated wounds were used as control for the treatment groups. The wounds were covered with an OpSite® polyurethane dressing (Smith & Nephew plc, London, UK). Wound healing was followed for 7 days or for 14 days. In the 14-day study at $7^{th}$ postoperative day wounds were photographed, fresh NFC hydrogel was added to the treated wounds, and wound dressings were changed.

Deep Wounds, Skin Grafts, and Graft Donor Sites

A 4 cm×5 cm skin graft was harvested with a Zimmer dermatome (Zimmer, Inc., Warsaw, Ind., USA) set at 30/1000 in. The harvested graft was meshed in 1:3 ratio with a skin graft mesher (Zimmer Inc). The donor site for the graft was further used as a partial thickness wound model. Half area of the donor site was covered with NFC hydrogel, and half was left untreated. Donor site was then covered with OpSite® (Smith & Nephew) dressing. Full thickness wounds (4 cm×4 cm) were made to the back skin of the pig. The split thickness skin grafts were placed on these wounds, and were fixed to the wound and to the healthy skin using surgical staples. NFC hydrogel (plant derived native non-modified NFC subjected to ion exchange treatment) was spread on top of the graft, and control wound was left untreated. The wounds were covered with Mepitel® (Mölnlycke, Gothenburg, Sweden) and an OpSite® (Smith & Nephew) polyurethane dressing. Wound healing was followed for 7 days or for 14 days. In the 14-day study at 7th postoperative day wounds were photographed, fresh NFC hydrogel was added to the treated wounds, and wound dressings were changed.

Histological Sections and Analysis

Wounds were either collected at day 7 or at day 14 after wounding. Samples were fixed in formaldehyde, and were paraffin embedded. Histological sections of samples were stained with hematoxylin and eosin, and were analyzed under light microscope. Morphometric analysis of wound size was carried out using the ImageJ program (http://rsb.info.nih.gov/ij/).

Ethical Issues

All animals were maintained and treated in accordance with the Principles of Laboratory Animal Care (NIH publications No. 8623, revised 1985). This study was approved by the Provincial State Office of Southern Finland (ESLH-2009-03831/Ym-23).

Results

Biopsy Wounds

Figure 5A:
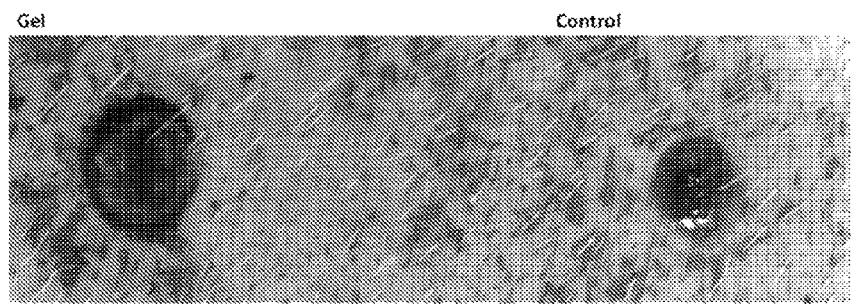
FIG. 5 illustrates the difference between NFC hydrogel-treated (left) and control (right) wounds after the 7-day follow-up, Example 3. The baseline fresh wounds are shown in FIG. 5B and in FIG. 5A are shown same wounds after 7 days.
Figure 5B:
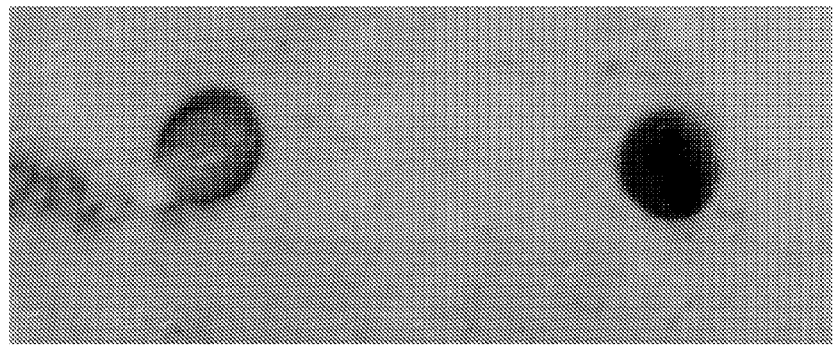
Figure 6:
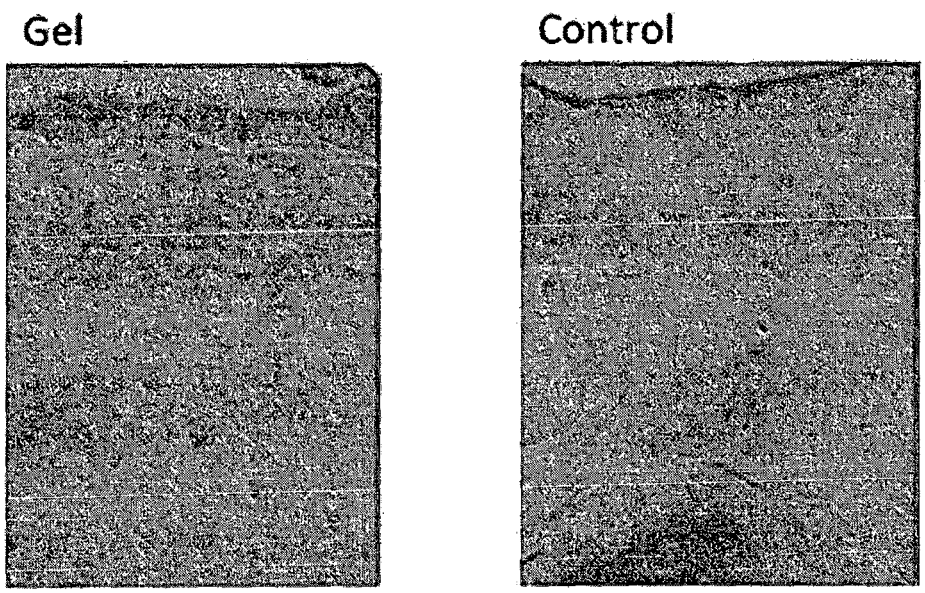
FIG. 6 presents histological sections of the wounds of Example 3.

FIGS. 5A and 5B show the difference between NFC hydrogel treated and control wounds after the 7-day follow-up, NFC treated on the left and control on the right. The baseline fresh wounds are shown in FIG. 5B. NFC hydrogel treated wounds presented with a dramatically reduced wound contraction. Compared to controls the ruptured area was 65% larger in gel-treated wounds on $7^{th}$ postoperative day (FIG. 5A). Histological sections of the wounds are shown in FIG. 6.

Deep Wounds with STSG

Figure 7A:
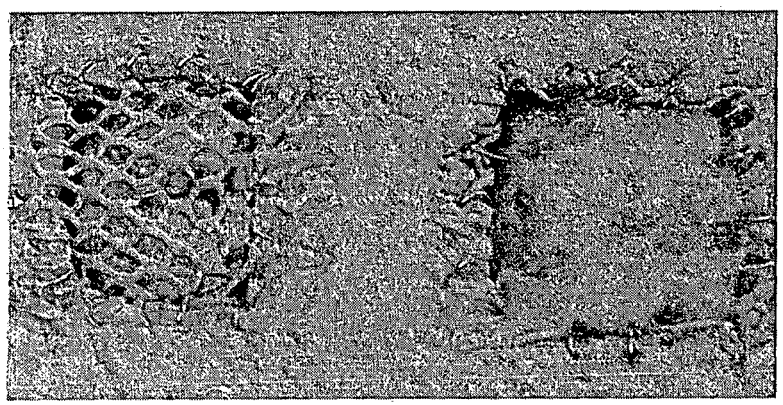
FIG. 7A shows the gross morphology of the wounds (control on left and hydrogel on right) at day 0, and FIG. 7B at day 7 after wounding (hydrogel on left and control on right), Example 3.
Figure 7B:
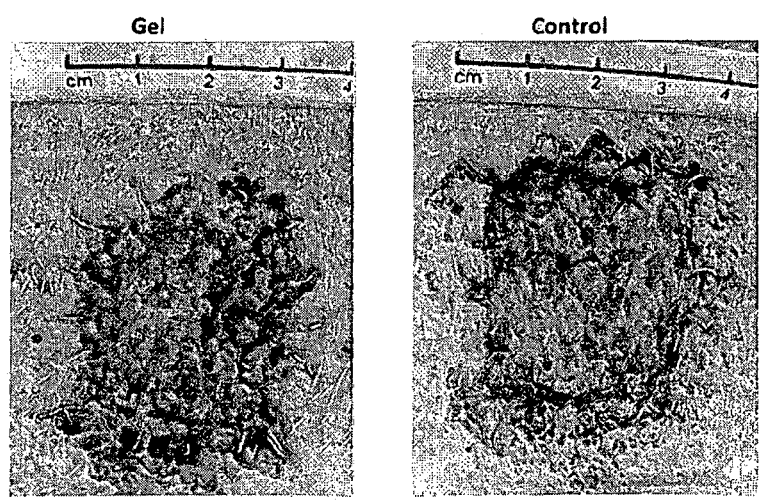
FIG. 7.
Figure 8:
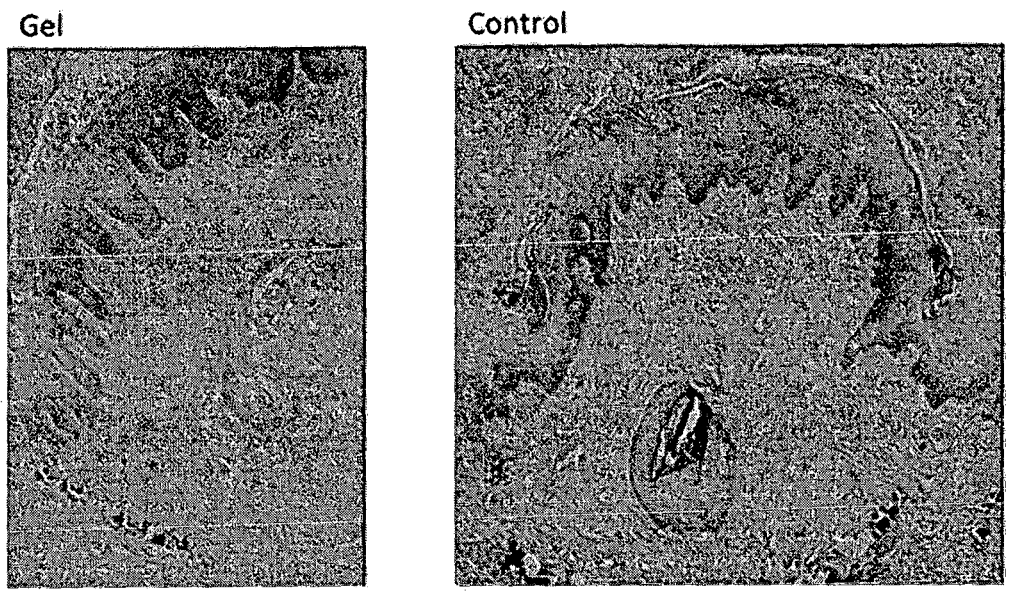
FIG. 8 shows histological analysis, revealing enhanced epithelial cell migration in wounds treated with NFC hydrogel, Example 3.

FIG. 7A (control on the left, gel on the right) shows the gross morphology of the wounds at day 0, and FIG. 7B at day 7 after wounding. Inhibition of wound and graft contraction is evident (NFC hydrogel treated wounds were 20% bigger in area compared to untreated control wounds). Histological analysis revealed enhanced epithelial cell migration in wounds treated with NFC hydrogel (FIG. 8). Some giant cells were observed suggesting a normal local reaction to foreign material.

Skin Graft Donor Site Wounds

Figure 9:
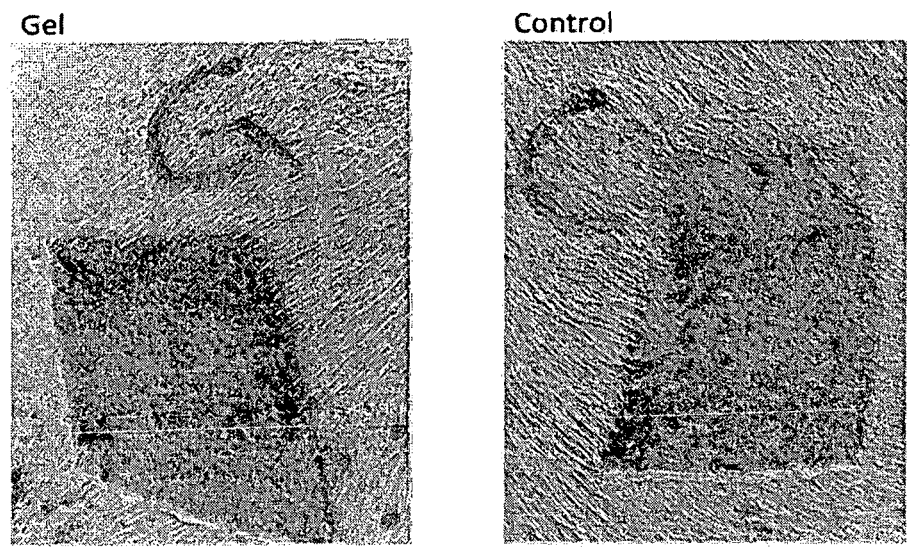
FIG. 9 illustrates gross morphological analysis of skin graft donor site, demonstrating at least equal rate of epithelialization with NFC hydrogel in comparison with untreated area, Example 3.
Figure 10A:
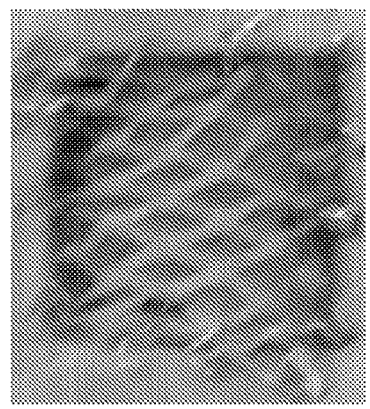
FIG. 10 shows baseline fresh control wound with graft, and after the 14-day follow-up, as well as a histological section of the wound, Example 3.
Figure 10B:
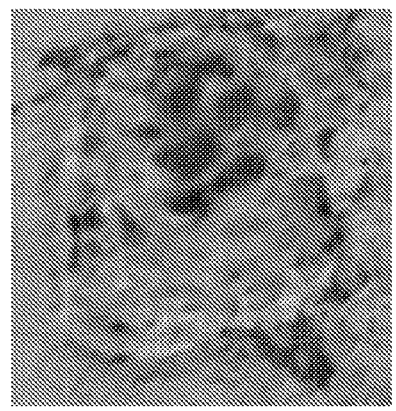
Figure 10C:
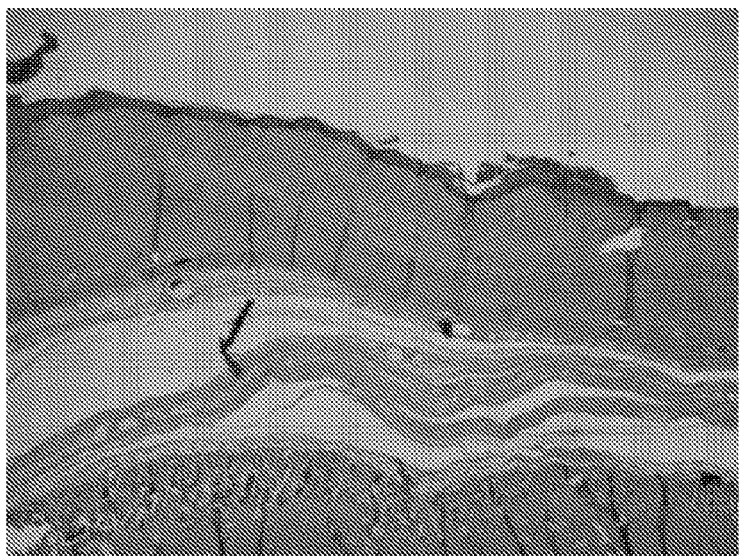
Figure 11A:
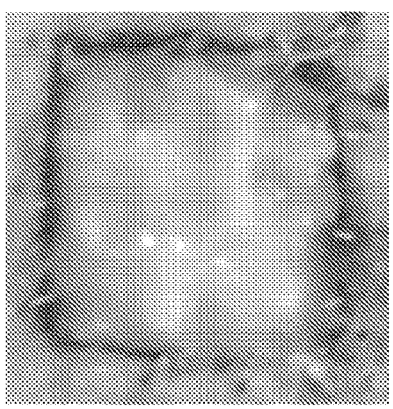
FIG. 11 shows baseline fresh NFC hydrogel treated wound with graft, and after the 14-day follow-up, as well as a histological section of the wound, Example 3.
Figure 11B:
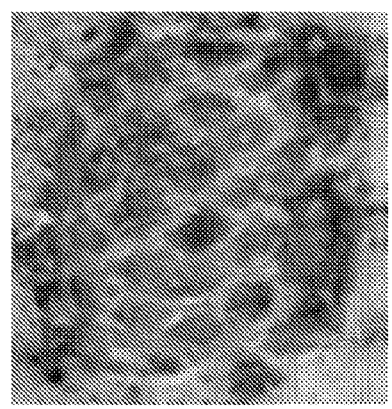
Figure 11C:
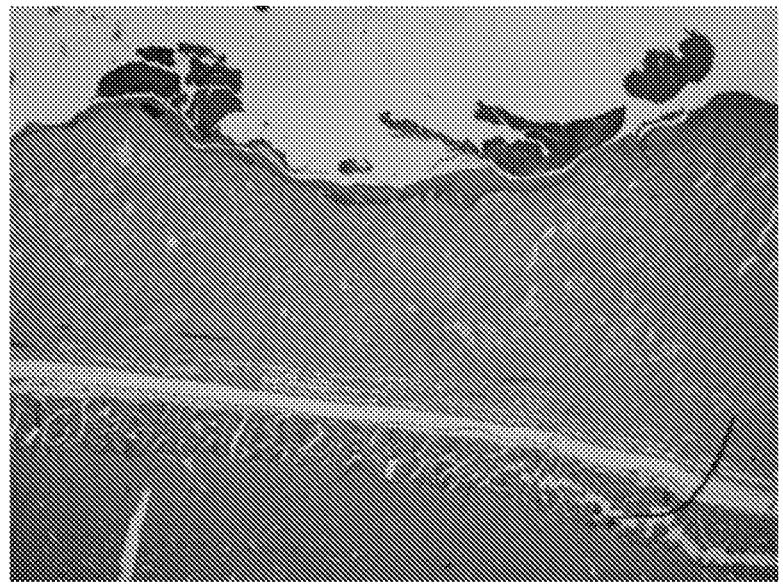

Gross morphological analysis of skin graft donor site demonstrated at least equal rate of epithelialization with NFC hydrogel in comparison with untreated area (FIG. 9). FIGS. 10 and 11 show the difference between NFC hydrogel treated wounds with graft and control wounds (without hydrogel) with graft after the 14-day follow-up. The baseline fresh wounds are shown in FIGS. 10a (control) and 11a (NFC hydrogel treated), and FIGS. 10b (control) and 11b (NFC hydrogel treated) show said wounds after 14 days. NFC hydrogel treated wounds presented with a dramatically reduced wound contraction after 14 days. Compared to controls the ruptured area was significantly larger in NFC gel-treated wounds on 14th postoperative day (FIG. 10b, 11b). Histological sections of the wounds with graft are shown in FIGS. 10c (control) and 11c (NFC hydrogel treated), confirming the findings. These data shows also that NFC does not inhibit wound epithelialization in this setting.

All wounds were clear of any signs of infection.

The NFC hydrogel material effectively prevented wound contraction and contraction of the STSG. NFC hydrogel applied on top of the graft showed no adverse effect on epithelialization.

These findings indicate that NFC hydrogel controls and inhibits contraction as seen with STSG application, and can prevent formation of contraction-induced fibrosis and movement restriction when applying STSG therapy in patients.

Example 4

Effect of NFC Hydrogels in the Prevention of Contraction in Porcine Model

In this example the effect of NFC hydrogels was compared with commercially available hydrogel Purilon in wound contraction test. NFC hydrogel manufactured from native cellulose and NFC hydrogel (transparent) manufactured from anionic cellulose were used as test materials.

The reference material Purilon gel was analyzed with a rheometer. The flow profile was measured directly for the 10 wt % product using similar measurement set-up as with NFC materials. The Purilon gel shows similar type of flow behavior as NFC gels, i.e. high zero shear viscosity (70 000

Pa s) and high yield stress (150 Pa). These values are comparable to NFC hydrogels at concentrations 1.5 to 3 wt %.

Figure 12:
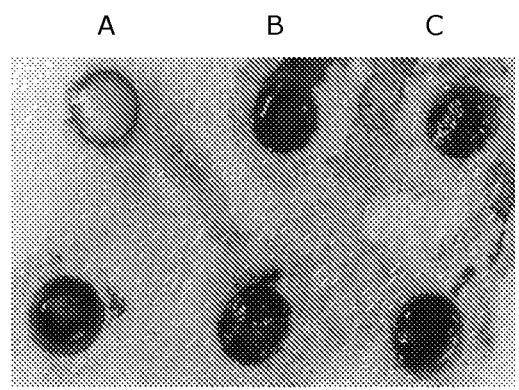
FIG. 12 presents a photo of biopsy wounds on day 0 after treatment with NFC, Purilon, and control, Example 4.
Figure 13:
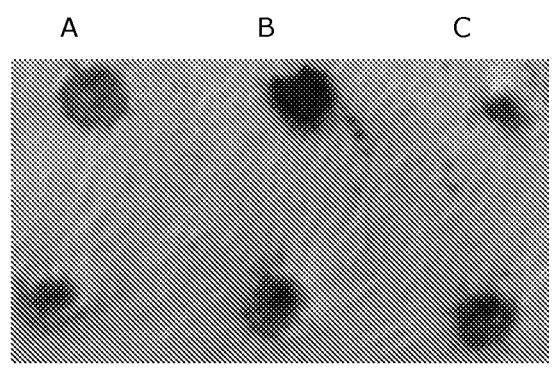
FIG. 13 presents a photo of biopsy wounds on day 14 after treatment with NFC, Purilon, and control, Example 4. The contraction percentage was calculated and presented for each test graphically. The results are shown in FIG. 14.
Figure 14:
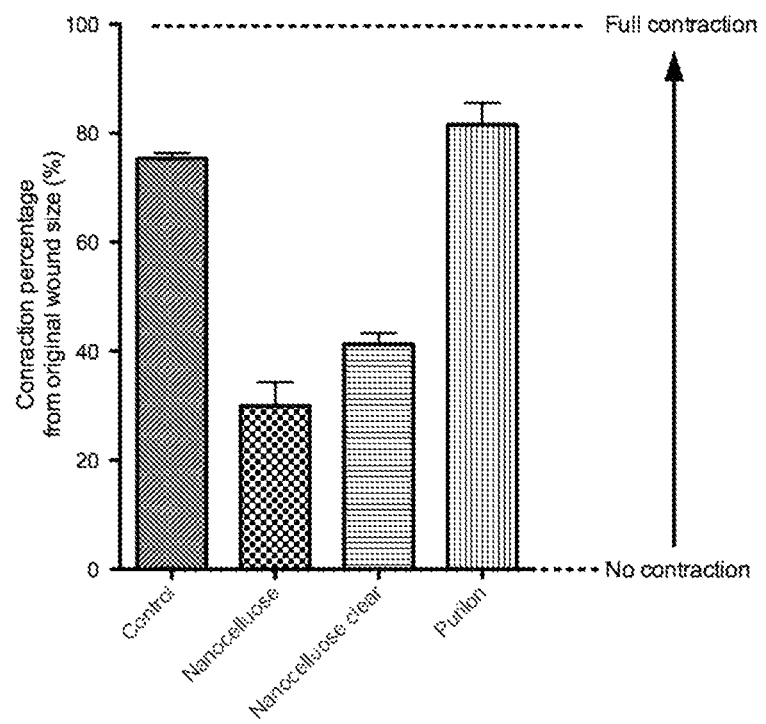
FIG. 14 illustrates graphically the calculated contraction percentage for each sample in Example 4.

The tests were carried out as described in Example 3, biopsy wound tests in 8 mm full thickness wounds. On day 0 biopsy wounds were filled with NFC hydrogel (A), NFC transparent hydrogel (B, F) and Purilon (C, E), untreated wound was used as control (D) (see FIG. 12). Contraction was followed for 14 days, (see FIG. 13), the contraction percentage was calculated and presented for each test graphically. The results are shown in FIG. 14.

Photographs and morphometric analysis show that NFC hydrogel inhibits wound contraction, whereas control wound and Purilon-treated wounds contract significantly at 14 days of follow-up.

The present invention has been described herein with reference to specific embodiments. It is, however clear to those skilled in the art that the invention may be varied within the scope of the claims.

The invention claimed is:

1. A method for the control and prevention of scarring and/or contraction in connection with wound healing or tissue repair in a subject in need thereof, the method comprising contacting a wound or a mucous membrane or tissue in the subject with an effective amount of a mechanically disintegrated nanofibrillar polysaccharide hydrogel, wherein said nanofibrillar polysaccharide hydrogel has yield stress between 0.1 and 50 Pa in water at 0.5 wt % concentration, wherein the nanofibrillar polysaccharide hydrogel comprises polysaccharide selected from plant-derived celluloses, derivatives thereof, or combinations thereof.

2. The method according to claim 1, wherein the wound is a skin wound, a burn wound, a chronic wound, a wound in mucous membrane, an ulcer or a wound in tendon.

3. The method according to claim 2, wherein the wound is at a donor and/or a recipient site, which in connection with therapy involving skin grafts is contacted with the nanofibrillar polysaccharide hydrogel, or nanofibrillar polysaccharide hydrogel is used in connection with flap technique.

4. The method of claim 1, wherein the nanofibrillar polysaccharide comprises polysaccharide selected from a cellulose, a hemicellulose, a chitin, a chitosan, an alginate, a pectin, an arabinoxylan, and derivatives or combinations thereof.

5. The method of claim 1, wherein the nanofibrillar polysaccharide hydrogel comprises polysaccharide nanofibrils and/or nanofibril bundles having number average diameter between 1 and 500 nm, preferably between 2 and 200 nm.

6. The method of claim 1, wherein said nanofibrillar polysaccharide hydrogel has storage modulus between 1 and 50 Pa in water at 0.5 wt % concentration.

7. The method of claim 1, wherein the nanofibrillar polysaccharide hydrogel has yield stress between 2 and 15 Pa in water at 0.5 wt % concentration.

8. The method of claim 1, wherein the nanofibrillar polysaccharide hydrogel has zero-shear viscosity between 100 and 100 000 Pas in water at 0.5 wt % concentration.

9. The method of claim 8, wherein the nanofibrillar polysaccharide hydrogel has zero-shear viscosity between 5000 and 50 000 Pas, in water at 0.5 wt % concentration.

10. The method of claim 1, wherein the nanofibrillar polysaccharide is native nanofibrillar cellulose or anionic nanofibrillar cellulose.

11. The method of claim 1, wherein the nanofibrillar polysaccharide hydrogel contains from 0.01 to 30 wt % of nanofibrillar polysaccharide or any combinations thereof.

12. The method of claim 11, wherein the nanofibrillar polysaccharide hydrogel contains from 0.05 to 5 wt % of nanofibrillar polysaccharide or any combinations thereof.

13. The method of claim 1, wherein the nanofibrillar polysaccharide hydrogel comprises one or more additional components selected from bioactive agents, cells and nutritional agents.

14. The method of claim 1, wherein the nanofibrillar polysaccharide hydrogel has a backing material attached thereto, or it is incorporated on a support.

15. The method of claim 1, wherein the nanofibrillar polysaccharide hydrogel is incorporated in a gauze or nonwoven material.

16. The method of claim 1, wherein the chronic wound is selected from a neuropathic ulcer, a pressure sore, a venous stasis ulcer, and an ulcer caused by diabetes or its complications.

17. The method of claim 16, wherein the wound is a diabetic ulcer and the nanofibrillar polysaccharide hydrogel is contacted with the wound in connection with split thickness skin graft therapy.

18. The method of claim 1, wherein the wound is in contacted with the nanofibrillar polysaccharide hydrogel in connection with a skin graft.

19. The method of claim 1, wherein said nanofibrillar polysaccharide hydrogel has a storage modulus between 3 and 20 Pa in water at 0.5 wt % concentration.

* * * * *